(12) United States Patent
Bonnet et al.

(10) Patent No.: US 7,803,968 B2
(45) Date of Patent: Sep. 28, 2010

(54) METHOD FOR MAKING CARBOXYLIC ACIDS

(75) Inventors: Didier Bonnet, Lyon (FR); Daniel Amoros, Venissieux (FR); Jean-Pierre Simonato, Sassenage (FR); Frédéric Augier, Saint Symphorien D'Ozon (FR); Maria Ignez Broglio, Lyon (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 1332 days.

(21) Appl. No.: 10/533,227

(22) PCT Filed: Oct. 28, 2003

(86) PCT No.: PCT/FR03/03196

§ 371 (c)(1),
(2), (4) Date: Oct. 3, 2005

(87) PCT Pub. No.: WO2004/041768

PCT Pub. Date: May 21, 2004

(65) Prior Publication Data

US 2006/0094900 A1    May 4, 2006

(30) Foreign Application Priority Data

Oct. 30, 2002  (FR) .................................. 02 13579

(51) Int. Cl.
*C07C 51/31* (2006.01)
(52) U.S. Cl. .................................................. 562/543
(58) Field of Classification Search ........................ None
See application file for complete search history.

(56) References Cited

U.S. PATENT DOCUMENTS

| 2,552,198 | A | * | 5/1951 | Mayland et al. | 585/838 |
|---|---|---|---|---|---|
| 3,988,116 | A | * | 10/1976 | Robbins | 422/256 |
| 4,032,569 | A | * | 6/1977 | Onopchenko et al. | 562/543 |
| 4,120,902 | A | * | 10/1978 | Wu | 568/342 |
| 4,536,597 | A | * | 8/1985 | Pesa et al. | 562/522 |
| 4,954,260 | A | * | 9/1990 | Ludmer et al. | 210/634 |
| 5,321,157 | A | * | 6/1994 | Kollar | 562/543 |
| 5,756,837 | A | * | 5/1998 | Costantini et al. | 562/543 |
| 6,231,821 | B1 | * | 5/2001 | Boogers et al. | 423/22 |
| 6,307,100 | B1 | * | 10/2001 | Richardson et al. | 562/543 |
| 2003/0032825 | A1 | * | 2/2003 | Gaige et al. | 554/121 |

* cited by examiner

*Primary Examiner*—Melvin C Mayes
*Assistant Examiner*—Stefanie Cohen
(74) *Attorney, Agent, or Firm*—Buchanan Ingersoll & Rooney PC

(57) ABSTRACT

The present invention relates to a process for producing carboxylic acids. It relates more particularly to a process for producing carboxylic acids by oxidation of a hydrocarbon with oxygen or a gas containing oxygen, and even more particularly to the oxidation of cyclohexane to adipic acid. The invention relates to a process for producing carboxylic acids by oxidation with oxygen or a gas containing oxygen of a cycloaliphatic hydrocarbon in the presence of an oxidation catalyst and of a monocarboxylic oxidation solvent that is lipophilic in nature, comprising a step of extraction of the dicarboxylic acids formed in the oxidation step, consisting in carrying out, in liquid phase, an extraction of the diacids using water.

16 Claims, No Drawings

METHOD FOR MAKING CARBOXYLIC ACIDS

This application is an application under 35 U.S.C. Section 371 of International Application Number PCT/FR2003/003196 filed on Oct. 28, 2003.

The present invention relates to a process for producing carboxylic acids.

It relates more particularly to a process for producing carboxylic acids by oxidation of a hydrocarbon with oxygen or a gas containing oxygen, and even more particularly to the oxidation of cyclohexane to adipic acid.

Adipic acid is an important chemical compound used in many fields. Thus, adipic acid can be used as an additive in many products, both in the area of foods and in concrete. However, one of the most important uses is its application as a monomer in the production of polymers, including polyurethanes and polyamides.

Several processes for producing adipic acid have been proposed. One of the most important, used industrially on a large scale, consists in oxidizing, in one or two step(s), cyclohexane to a mixture of cyclohexanol/cyclohexanone with a gas containing oxygen or with oxygen. After extraction and purification of the cyclohexanol/cyclohexanone mixture, these compounds are oxidized in particular to adipic acid with nitric acid. However, this process has a major drawback associated with the formation of nitrous vapour.

Many studies have been carried out in order to develop a process for oxidizing hydrocarbons with oxygen or a gas containing oxygen, that makes it possible to directly obtain carboxylic acids, mainly adipic acid.

These processes are described in particular in patents FR 2,761,984, FR 2,791,667, FR 2,765,930 and U.S. Pat. No. 5,294,739.

Generally, the reaction is carried out in a solvent medium, the solvent being a monocarboxylic acid such as acetic acid. However, such a process has not, for the moment, been the subject of any substantial industrial development since the separation of adipic acid and of acetic acid requires considerable process steps in order to obtain, firstly, a highly pure adipic acid compatible with the demands required for the production of polyamide, in particular for textile applications, and, secondly, recovery and recycling of the acetic acid that are as complete as possible so as not to economically penalize the process.

In order to attempt to remedy these drawbacks, novel solvents have been sought and proposed for carrying out the oxidation of cyclohexane with oxygen. Thus, monocarboxylic acid solvents that are lipophilic in nature have been proposed, in particular in patent FR 2806079. The acids have the advantage of a low affinity with adipic acid and of not being soluble in solvents for adipic acid, such as water. Consequently, the recovery of the adipic acid in the aqueous phase present at the end of the oxidation step can be carried out more readily with limited entrainment of the mono-carboxylic solvent.

However, these solvents can have high melting points, in particular above ambient temperature, which means a more complex extraction process or that the extraction or separation processes must be carried out at high temperatures.

One of the aims of the present invention is to propose an effective and easy process for producing carboxylic acids by oxidation of hydrocarbons using oxygen or a gas containing oxygen, in the presence of a solvent that is lipophilic in nature, which process uses a step consisting of effective extraction of the acids formed and complete recycling of the oxidation solvent.

To this effect, the invention proposes a process for producing dicarboxylic acids by oxidation with oxygen or a gas containing oxygen of a cycloaliphatic hydrocarbon in the presence of an oxidation catalyst and of an oxidation solvent that is lipophilic in nature, characterized in that it comprises a step of extraction of the dicarboxylic acids formed in the oxidation step, consisting in carrying out, in liquid phase, an extraction of the diacids using an extraction solvent in which at least the oxidation solvent and the cycloaliphatic hydrocarbon are insoluble.

As a solvent that is lipophilic in nature, monocarboxylic compounds are preferred.

For the purpose of the patent, the products are considered to be insoluble in the extraction solvent if their solubility in said solvent, measured at 90° C. and under atmospheric pressure, is less than or equal to 10% by weight relative to the solvent.

According to one characteristic of the invention, the extraction of the diacids formed is carried out in a countercurrent-flow liquid/liquid extraction column. The extraction solvent is advantageously chosen from the group comprising polar solvents, water and alcohols such as methanol. The preferred solvent is water or a solution containing mainly water.

As liquid-liquid extraction columns that are suitable for the invention, the various principles and devices commonly used in industrial processes can be used. Thus, columns with mechanical agitation using a disc or rotor, columns using pulse technology, static columns with perforated trays or static packed columns are suitable. Preferably, columns with mechanical agitation are preferred. Of course, this extraction can be carried out in a single extraction column or in several extraction columns mounted in series and/or in parallel without nevertheless departing from the context of the invention. It is also possible to use one or more extraction columns in combination with washing-settling devices.

According to a preferred novel characteristic of the invention, the reaction medium derived from the oxidation step is fed into the extraction step under given temperature and pressure conditions so as to maintain the cycloaliphatic hydrocarbon in the liquid state.

Advantageously, the extraction of the diacids is carried out under given temperature and pressure conditions so as to maintain the cycloaliphatic hydrocarbon in the liquid state.

The maintaining of the hydrocarbon in the liquid state during the extraction phase makes it possible to maintain the oxidation solvent in the solubilized state, or to maintain a homogeneous solution between the hydrocarbon and the oxidation solvent. Thus, it is possible to carry out the extraction of the diacids under temperature conditions that are less severe, in particular within a temperature range below the solidifying temperature or crystallization temperature of the oxidation solvent, or at a temperature that prevents any precipitation of the oxidation solvent.

In a particular embodiment of the invention, a second extraction solvent is fed into the extraction column in a direction countercurrent to the first extraction solvent. This second solvent is a solvent for the oxidation solvent such as monocarboxylic acids that are lipophilic in nature and is not miscible with the first extraction solvent. This double extraction allows a virtually complete recovery of the oxidation solvent and recycling thereof.

This second solvent is chosen from apolar solvents having a solubility in the first extraction solvent of less than or equal to 5% by weight relative to the first extraction solvent, this solubility being measured at a temperature of 20° C. under atmospheric pressure. Advantageous, this second solvent is chosen from acyclic or cyclic, saturated hydrocarbons, and aromatic hydrocarbons. Advantageously, this second solvent is the hydrocarbon to be oxidized, in particular cyclohexane. Advantageously, the supply of this second solvent represents at least partially the supply of hydrocarbon to be oxidized in the oxidation process of the invention when it is a continuous process.

In a preferred embodiment of the invention, the reaction medium is supplied at an intermediate position on the column, and the first extraction solvent and the second extraction solvent are supplied, respectively, at each end of the column.

The reaction medium is generally obtained from the oxidation, with oxygen or a gas containing oxygen, of an arylaliphatic hydrocarbon, more particularly of a cycloaliphatic arylaliphatic hydrocarbon such as cyclohexane or cyclododecane. The oxidation reaction is generally carried out in the presence of a solvent. The solvent may be very varied in nature insofar as it is not substantially oxidizable under the reaction conditions.

According to a preferred characteristic of the invention, the solvent is chosen from carboxylic acids that are lipophilic in nature.

The expression "lipophilic acid compound that is suitable for the invention" is intended to mean aromatic, aliphatic, arylaliphatic or alkylaromatic compounds comprising at least 6 carbon atoms, that may comprise several acid functions and that have low water-solubility, i.e. a solubility of less than 10% by weight at ambient temperature (10° C.-30° C.).

As lipophilic organic compounds, mention may be made, for example, of hexanoic acid, heptanoic acid, octanoic acid, 2-ethylhexanoic acid, nonanoic acid, decanoic acid, undecanoic acid, dodecanoic acid, stearic acid (octadecanoic acid) and their permethylated derivatives (complete substitution of the hydrogens of the methylene groups with the methyl group), 2-octadecylsuccinic acid, 3,5-ditert-butyl-benzoic acid, 4-tert-butylbenzoic acid, 4-octylbenzoic acid, tert-butyl hydrogen orthophthalate, naphthenic or anthracenic acids substituted with alkyl groups, preferably of tert-butyl type, substituted derivatives of phthalic acids, and fatty diacids such as dimer fatty acid. Mention may also be made of the acids belonging to the above families and bearing various electron-donating substituents (groups with a hetero atom of the O or N type) or electron-withdrawing substituents (halogens, sulphonimides, nitro groups, sulphonato groups, or the like).

In general, the lipophilic acid solvent is chosen so as to advantageously obtain a homogeneous phase under the temperature and pressure conditions at which the oxidation reaction is carried out. For this, it is advantageous for the solubility of the solvent in the hydrocarbon or the reaction medium to be at least greater than 2% by weight, and for at least one homogeneous liquid phase comprising at least some of the hydrocarbons to be oxidized and some of the solvent to be formed.

Advantageously, the solvent is chosen from those with low water-solubility, i.e. that have a water-solubility of less than 10% by weight at ambient temperature (10-30° C.).

However, it is possible, without departing from the context of the invention, to use a solvent having a water-solubility that is greater than that indicated above, if the partition coefficient for this compound between the organic phase(s) of the reaction medium consisting essentially of the hydrocarbon to be oxidized, the oxidation intermediates and the nonorganic phase comprising the water formed during the oxidation reaction makes it possible to obtain a concentration of the solvent in said aqueous phase of less than 10% by weight.

The oxidation is in general carried out in the presence of a catalyst. This catalyst advantageously comprises a metal element chosen from the group comprising Cu, Ag, Au, Mg, Ca, Sr, Ba, Zn, Cd, Hg, Al, Sc, In, Tl, Y, Ga, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, lanthanides such as Ce, and combinations thereof.

These catalytic elements are used either in the form of compounds that are advantageously at least partially soluble in the liquid oxidation medium under the conditions under which the oxidation reaction is carried out, or are carried by, absorbed onto or attached to an inert support such as silica or alumina, for example.

The catalyst is preferably, in particular under the conditions under which the oxidation reaction is carried out:
   either soluble in the hydrocarbon to be oxidized,
   or soluble in the lipophilic acid compound,
   or soluble in the hydrocarbon/lipophilic acid compound mixture forming a homogeneous liquid phase under the conditions under which the reaction is carried out.

According to a preferred embodiment of the invention, the catalyst used is soluble in one of these media at ambient temperature or at the temperature for recycling of these media in a further oxidation.

The term "soluble" is intended to mean that the catalyst is at least partially soluble in the medium under consideration.

In the case of a heterogeneous catalyst, the catalytically active metal elements are supported or incorporated in or into a microporous or mesoporous mineral matrix, or in or into a polymeric matrix, or are in the form or organometallic complexes grafted onto an organic or mineral carrier. The term "incorporated" is intended to mean that the metal is an element of the carrier or that the process is carried out with complexes that are sterically trapped in porous structures under the conditions of the oxidation.

In a preferred embodiment of the invention, the homogeneous or heterogeneous catalyst consists of salts or complexes of metals of groups Ivb (the group of Ti), Vb (the group of V), VIb (the group of Cr), VIIb (the group of Mn), VIII (the group of Fe or Co or Ni) and Ib (the group of Cu) and cerium, alone or as a mixture. The preferred elements are, in particular, Mn and/or Co which can be used in combination with one or more elements chosen from the group comprising Cr, Zr, Hf, Ce and Fe. The concentrations of metal in the liquid oxidation medium range between 0.00001 and 5% (wt %), preferably between 0.001% and 2%.

Moreover, the concentration of solvent in the reaction medium is advantageously determined so as to have a molar ratio of the number of molecules of solvent and the catalytic element metal number of between 0.5 and 100 000, preferably between 1 and 5000.

The concentration of solvent in the liquid oxidation medium can vary within broad limits. Thus, it can be between 1 and 99% by weight relative to the total weight of liquid medium, more advantageously it can be between 2 and 50% by weight of the liquid medium.

It is also possible, without nevertheless departing from the context of the invention, to use the solvent in combination with another compound that may in particular have the effect of improving the productivity and/or the selectivity of the reaction of oxidation to adipic acid, and in particular the solubilization of the oxygen.

As examples of such compounds, mention may in particular be made of nitrites, hydroxyimide compounds, halogenated compounds, and more advantageously fluorinated compounds. As compounds that are more particularly suitable, mention may be made of nitrites such as acetonitrile or benzonitrile, imides belonging to the family described in European Patent EP 0824962, and more particularly N-hydroxysuccinimide (NHS) or N-hydroxyphthalimide (NHPI), halogenated derivatives such as dichloromethane, and fluorinated compounds such as:

- cyclic or acyclic, fluorinated or perfluorinated, aliphatic hydrocarbons,
- aromatic fluorinated hydrocarbons such as perfluorotoluene, perfluoromethylcyclohexane, perfluoroheptane, perfluorooctane, perfluorononane, perfluorodecaline, perfluoromethyldecaline, α,α,α-trifluorotoluene or 1,3-bis-(trifluoromethyl)benzene,
- perfluorinated or fluorinated esters such as alkyl perfluorooctanoates or alkyl perfluorononanoates,
- fluorinated or perfluorinated ketones such as perfluoroacetone,
- fluorinated or perfluorinated alcohols such as perfluorohexanol, perfluorooctanol, perfluorononanol, perfluorodecanol, perfluoro-tert-butanol, perfluoroisopropanol or 1,1,1,3,3,3-hexafluoro-2-propanol,
- fluorinated or perfluorinated nitriles such as perfluoroacetonitrile,
- fluorinated or perfluorinated acids such as trifluoromethylbenzoic acids, pentafluorobenzoic acid, perfluorohexanoic acid, perfluoroheptanoic acid, perfluorooctanoic acid, perfluorononanoic acid or perfluoroadipic acid,
- fluorinated or perfluorinated halides such as perfluoroiodooctane, or perfluorobromooctane,
- fluorinated or perfluorinated amines such as perfluorotripropylamine, perfluorotributylamine or perfluorotripentylamine.

The invention applies more particularly to the oxidation of cycloaliphatic compounds, such as cyclohexane or cyclododecane, to the corresponding linear diacids, adipic acid or dodecanoic acid.

According to a preferred embodiment of the invention, it relates to the direct oxidation of cyclohexane to adipic acid, with a gas containing oxygen, in a liquid medium and in the presence of a manganese catalyst, in particular a manganese- and cobalt-based catalyst.

The oxidation reaction is carried out at a temperature of between 50° C. and 200° C., preferably of between 70° C. and 180° C. It can be carried out under atmospheric pressure. However, it is generally carried out under a pressure so as to maintain the components of the reaction medium in the liquid form. The pressure can be between 10 kPa (0.1 bar) and 20 000 kPa (200 bar), preferably between 100 kPa (1 bar) and 10 000 kPa (100 bar).

The oxygen used may be in pure form or as a mixture with an inert gas such as nitrogen or helium. Air more or less enriched with oxygen may also be used. The amount of oxygen supplied to the medium is advantageously between 1 and 1000 mol per mole of compounds to be oxidized.

The oxidation process can be carried out continuously or according to a batch process. Advantageously, the liquid reaction medium that has left the reactor is treated according to known processes for, firstly, separating and recovering the diacid produced and, secondly, recycling the non-oxidized or partially oxidized organic compounds such as cyclohexane, cyclohexanol and/or -cyclohexanone, the catalyst and the acid compound.

It is advantageous to also use a compound that initiates the oxidation reaction, for instance a ketone, an alcohol, an aldehyde or a hydroperoxide. Cyclohexanone, cyclohexanol and cyclohexyl hydroperoxide, which are reaction intermediates in the case of the oxidation of cyclohexane, are all particularly indicated. In general, the initiator represents from 0.01% to 20% by weight of the weight of the reaction mixture used, without these proportions having a critical value. The initiator is especially useful during the initiation of the oxidation. It can be introduced from the beginning of the reaction.

The oxidation can also be carried out in the presence of water introduced from the initial stage of the process.

In these various embodiments, the carboxylic acid recovered after the liquid/liquid extraction step can be purified according to the usual techniques described in many documents, for example by crystallization and recrystallization from various solvents such as water, acetic acid or other organic solvents. Purification processes are in particular described in French Patents No. 2,749,299 and 2,749,300.

Similarly, if the catalyst is not entirely recycled with the organic phase, and is partly or completely extracted with the aqueous phase, it will be advantageously extracted from the aqueous phase by various techniques, such as liquid/liquid extraction, electrodialysis, or treatment on ion exchange resin, for example.

Moreover, the organic phase recovered from the reaction medium can be subjected to distillation operations in order to recycle the nonoxidized hydrocarbon, the various oxidation compounds such as the alcohols, the ketones, and the oxidation solvent. In addition, the organic phase can be subjected to a treatment in order to eliminate the esters, in particular before recycling of the solvent.

Other advantages and details of the invention will become apparent in view of the examples given below, only by way of indication.

EXAMPLE 1

Oxidation Step 522 g of cyclohexane, 55 g of tert-butylbenzoic acid and 6 g of cyclohexanone (initiator) are placed in a 1.5 l reactor. Manganese and cobalt are added in respective amounts of 50 and 20 ppm by mass.

The mixture is stirred at 130° C., 20 bar, for 150 min under a continuous stream of gas containing nitrogen and oxygen. After 35 l of oxygen have been consumed, a mixture of cyclohexane, of tert-butylbenzoic acid, of cyclohexanone, of cyclohexanol, of manganese and of cobalt is added continuously. A level sensor connected to a reactor emptying system makes it possible to keep the reactor level constant.

Extraction Step

After 3 hours of stabilized regime, a portion of 200 g of oxidation reaction mixture is isolated. A mass of 200 g of water is added to this fraction in a mixer maintained at 70° C. After agitation and then separation by settling out, two phases are recovered: a lower phase, referred to as aqueous phase, which contains essentially the diacids produced and the catalytic metals, and an upper phase, referred to as organic phase, which contains essentially cyclohexane, the tert-butylbenzoic acid, cyclohexanone, cyclohexanol and other by-products of the reaction.

Analysis of the two phases shows that 85% by weight of the adipic acid formed and present in the reaction mixture portion is recovered and extracted in the aqueous phase, and 99.3% by weight of the t-BBA is recovered in the organic phase.

EXAMPLE 2

The oxidation step is identical to that described in Example 1. However, the oxidation reaction medium withdrawn continuously from the reactor is fed into an agitated stage extraction column having a theoretical stage number of 10. The extraction column operates at a temperature of 100° C. under a pressure of 5 bar.

The column is fed at the level of an intermediate stage (fifth stage) with the oxidation reaction medium, with a flow rate corresponding to a feed of 1.11 kg/h of t-BBA and 1.09 kg/h of adipic acid at a temperature of 100° C. under a pressure of 5 bar.

The column is also fed, at the head of the column, with water with a flow rate of 1.62 kg/h and, at the foot of the column, with a flow of cyclohexane equal to 1.04 kg/h.

The organic phase recovered at the head of the column comprises 1.11 kg/h of t-BBA, 1.04 kg/h of cyclohexane and 0.007 kg/h of adipic acid.

The aqueous phase withdrawn at the foot of the column comprises 0.001 kg/h of t-BBA, 1.62 kg/h of water and 1.083 kg/h of adipic acid.

These trials clearly demonstrate that the process of the invention makes it possible to extract virtually all the adipic acid formed without entraining oxidation solvent. In fact, said solvent is almost entirely in the organic phase and may be recycled after, advantageously, a purification.

In addition, some of the adipic acid may be entrained in the organic phase in the form of esters. These may be treated before the recycling of the oxidation solvent.

The invention claimed is:

1. A process for producing dicarboxylic acids comprising:
   a) an oxidation step compromising producing a dicarboxylic acid by oxidizing a cycloaliphatic hydrocarbon starting material with oxygen or a gas containing oxygen in a reaction medium comprising an oxidation catalyst and a lipophilic oxidation solvent, and
   b) an extraction step comprising extracting the dicarboxylic acid formed in the oxidation step from said reaction medium in a countercurrent-flow liquid liquid extraction column using a first extraction solvent in which at least the oxidation solvent and the cycloaliphatic hydrocarbon starting material are insoluble and a second extraction solvent which is the cycloaliphatic hydrocarbon starting material.

2. The process according to claim 1, wherein the lipophilic oxidation solvent is a monocarboxylic acid.

3. The process according to claim 1, wherein the reaction medium derived from the oxidation step is fed into the extraction step under given temperature and pressure conditions so as to maintain the cycloaliphatic hydrocarbon in the liquid state.

4. The process according to claim 1, wherein the extraction step comprising extracting the dicarboxylic acids is carried out under given temperature and pressure conditions so as to maintain the cycloaliphatic hydrocarbon starting material in the liquid state.

5. The process according to claim 1, wherein the first extraction solvent is water or an alcohol.

6. The process according to claim 5, wherein the first extraction solvent is water.

7. The process according to claim 1, wherein the first and the second extraction solvents are fed into the countercurrent extraction column.

8. The process of claim 7, wherein the second extraction solvent is fed into the countercurrent extraction column in a direction countercurrent to the first extraction solvent.

9. The process according to claim 1, wherein the reaction medium is fed into the extraction column at an intermediate position between the two ends of the column.

10. The process according to claim 1, wherein the cycloaliphatic hydrocarbon starting material is a cycloalkane.

11. The process according to claim 1, wherein the cycloaliphatic hydrocarbon starting material is a cycloalkane selected from cyclohexane or cyclododecane.

12. The process of according to claim 1, wherein the lipophilic oxidation solvent is a monocarboxylic acid that is lipophilic in nature, having from 7 to 20 carbon atoms.

13. The process of according to claim 1, wherein the lipophilic oxidation solvent is selected from the group consisting of hexanoic acid, heptanoic acid, octanoic acid, 2-ethylhexanoic acid, nonanoic acid, decanoic acid, undecanoic acid, dodecanoic acid, stearic acid (octadecanoic acid), 2-octadecylsuccinic acid, 1,5-ditert-butylbenzoic acid, 4-tert-butylbenzoic acid, 4-octylbenzoic acid, tert-butyl hydrogen orthophthalate, a naphthenic acid substituted with alkyl group, an anthracenic acid substituted with alkyl groups, a substituted derivative of a phthalic acid, or a fatty diacid.

14. The process according to claim 1, wherein the catalyst is a transition metal.

15. The process according to claim 14, wherein the catalyst comprises manganese and the catalyst is used in combination with a co-catalyst comprising cobalt, chromium, zirconium, hafnium or iron alone or in combination.

16. The process according to claim 1, wherein the dicarboxylic acids produced are adipic acid, succinic acid, glutaric acid, dodecanedioic acid or a mixture thereof.

* * * * *